(12) United States Patent
Ono et al.

(10) Patent No.: US 6,462,078 B1
(45) Date of Patent: Oct. 8, 2002

(54) EPOXYVIBSANIN B

(75) Inventors: Mitsunori Ono, Lexington, MA (US); Yumiko Wada, Waltham, MA (US); Naoto Yamaguchi, Lexington, MA (US); Jifeng Duan, Bedford, MA (US)

(73) Assignee: Shionogi Bioresearch Corp., Lexington, MA (US)

( * ) Notice: Subject to any disclaimer, the term of this patent is extended or adjusted under 35 U.S.C. 154(b) by 0 days.

(21) Appl. No.: 10/056,699

(22) Filed: Jan. 25, 2002

Related U.S. Application Data

(60) Provisional application No. 60/264,914, filed on Jan. 29, 2001.

(51) Int. Cl.⁷ .................... A61K 31/336; C07D 303/14; C07D 303/32

(52) U.S. Cl. ......................................... 514/475; 549/546

(58) Field of Search ............................ 514/475; 549/546

(56) References Cited

PUBLICATIONS

Yoshiyasu Fukuyama, et al. Chemical Conversion of Vibsanin C to Vibsanin E and Structure of 3–Hydroxyvibsanin E from *Viburnum awabuki*. J. Nat. Prod. 62:337–339, 1999.

Kazuyoshi Kawazu. Isolation of Vibsanins A, B, C, D, E, and F from *Viburnum odoratissimum*. Agric. Biol. Chem. 44(6):1367–1372, 1980.

Yoshiyasu Fukuyama, et al. Abolute Structure of Vibsanins B and C, and Their Chemical Correlation. Tetrahedron Letters 38(8):1435–1438, 1997.

Keiichi Fukuyama, et al. Structure and Absolute Configuration of Visanine E isolated from Leaves of *Viburnum odoratissimum* Ker. J.C.S. Perkin III, pp. 1701–1703, 1980.

Miwa Kubo, et al. Vibsane–type Diterpenes from Taiwanese *Viburnum odoratissimum*. Chem. Pharm. Bull. 49(2):242–245, 2001.

*Primary Examiner*—Ba K. Trinh
(74) *Attorney, Agent, or Firm*—Fish & Richardson P.C.

(57) ABSTRACT

This invention relates to a new compound, epoxyvibsanin B, which can be used to treat an IL-12 overproduction-related disorder such as an inflammatory disease.

5 Claims, No Drawings

EPOXYVIBSANIN B

RELATED APPLICATIONS

This application claims priority to U.S. provisional application No. 60/264,914, filed on Jan. 29, 2001, the contents of which are incorporated herein by reference.

BACKGROUND OF THE INVENTION

Interleukin-12 (IL-12) is a pivotal cytokine that mediates IL-12 receptors for producing proinflammatory cytokines, or promotes specific lymphocyte responses. One of its key roles is to promote type 1 T helper cell (Th1) responses and, hence, cell-mediated immunity. Overproduction of IL-12 will cause excessive Th1 responses, which may result in inflammatory disorders, such as autoimmune diseases. Gately et al. 1998, Annu Rev Immunol. 16, 495. IL-12 is therefore an ideal target for pharmacological intervention in the therapy of inflammatory diseases caused by excessive proliferation of Th1 cells. Trembleau et al. 1995; Immunol. Today 16, 383, and Adorini et al. 1997; Chem. Immunol. 68, 175. Overproduction of IL-12 and the resultant Th1 type immune responses can be suppressed with several pharmacological approaches including modulation of intracellular cyclic AMP levels, and inhibition of glucocorticoids and nuclear factor-kappaB. Hasko et al. 1999, Br. J. Pharmacol 127, 1295. It is desirable to identify a new compound for treatment of IL-12 overproduction-related disorders.

SUMMARY OF THE INVENTION

This invention is based on the identification of a new compound from a library of plant extracts, which were screened for their abilities to inhibit IL-12 production.

An aspect of this invention relates to the compound, epoxyvibsanin B, of the formula:

This compound can be either synthesized from organic chemicals or isolated from a natural source, e.g., *Caprifoliaceae vibrunum Awabuki*.

Another aspect of this present invention relates to a method of treating an IL-12 overproduction-related disorder with epoxyvibsanin B. The method includes administering to a subject in need thereof an effective amount of this compound.

Epoxyvibsanin B is formulated into a pharmaceutical composition before it is administered to a subject in need of treatment of an IL-12 overproduction-related disorder, which includes inflammatory (both acute and chronic) such as autoimmune diseases. Thus, also within the scope of the present invention is a pharmaceutical composition that contains an effective amount of epoxyvibsanin B and a pharmaceutically acceptable carrier for use in treatment of IL-12 overproduction-related disorders. The present invention also encompasses the use of epoxyvibsanin B for the manufacture of a medicament for treatment of the above-mentioned disorders.

Other advantages or features of the present invention will be apparent form the following detailed description thereof.

DETAILED DESCRIPTION OF THE INVENTION

The compound of the present invention, epoxyvibsanin B, can be isolated from *Caprifoliaceae vibrunum Awabuki* by the following procedure.

*Caprifoliaceae vibrunum Awabuki* leaves are collected from Miami (Fla., USA), suspended in an organic solvent, such as ethanol, and ground with a blender. The resultant solution is filtered to remove solid matter and the filtrate is dried under a reduced pressure, or by a flash evaporator, at a temperature of lower than 45° C., to produce a solid extract. Another organic solvent, such as ethyl acetate, is added to this solid extract to produce a liquid extract. This step is repeated several times. The liquid extracts are combined and dried under reduced pressure to produce another solid extract. To the solid extract, another organic solvent, such as methanol, is added again to produce another liquid extract. The step is repeated several times and all the liquid extracts are combined. The liquid extract thus obtained is dried using a flash evaporator to produce a further enriched solid extract. This solid extract is subsequently passed through a solid phase extraction column (SepPak $C_{18}$). A mixture of water and acetonitrile is used as the developing solvent and the elutant is fractionized. Each fraction is tested for an activity of inhibiting IL-12 production. The fractions having the activities are collected, combined and dried under reduced pressure to give solid matter. Then, the column is eluted again with the developing solvent, and more solid matter is thus obtained following the just-described procedures. The solid matter is further purified by high pressure liquid chromatography (HPLC) using a reversed phase column, with a mixture of water and acetonitrile as the developing solvent. The elutent fractions containing epoxyvibsanin B are collected again and dried under reduced pressure to produce pure epoxyvibsanin B as white powder.

Within the scope of this invention is epoxyvibsanin B, as well as a pharmaceutical composition that has an effective amount of epoxyvibsanin B for treating IL-12 overproduction-related disorders, including inflammatory such as autoimmune diseases (e.g., autoimmune diseases such as rheumatoid arthritis, psoriasis, diabetis type 1, and multiple scloresis). An effective amount of epoxyvibsainin B is defined as the amount of the compound which, upon administration to a subject in need of treatment of inflammatory such as autoimmune diseases, is required to confer therapeutic effect on the treated subject. The interrelationship of dosages for animals and humans (based on milligrams per meter squared of body surface) is described by Freireich et al., Cancer Chemother. Rep. 1966, 50, 219. Body surface area may be approximately determined from height and weight of the patient. See, e.g., Scientific Tables, Geigy Pharmaceuticals, Ardley, New York, 1970, 537. An effective amount of epoxyvibsanin B can range from about 0.1 mg/kg to about 50 mg/kg. Effective doses will also vary, as recognized by those skilled in the art, dependant on route of administration, excipient usage, and the possibility of co-usage with other therapeutic treatments such as the use of other anti-inflammatory agents.

Epoxyvibsanin B can be formulated into dosage forms for other routes of administration utilizing conventional methods. For example, it can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of epoxyvibsanin B with a solid carrier and a lubricant. Examples of solid carriers include starch and sugar bentonite. Epoxyvibsanin B can also be administered in a form of a hard shell tablet or a capsule containing a binder, e.g., lactose or mannitol, a conventional filler, and a tableting agent.

The pharmaceutical composition may be administered via the parenteral route, including orally, topically, subcutaneously, intraperitoneally, intramuscularly, and intravenously. Examples of parenteral dosage forms include aqueous solutions, isotonic saline or 5% glucose of the active agent, or other well-known pharmaceutically acceptable excipient. Solubilizing agents such as cyclodextrins, or other solubilizing agents well-known to those familiar with the art, can be utilized as pharnnaceutical excipients for delivery of the therapeutic compound.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Isolation of Epoxyvibsanin B from a Natural Source 2 kg of fresh *Caprifoliaceae vibrunum Awabuki* leaves collected at Miami, Fla. were suspended in 3 L of ethanol, ground with a blender, and soaked at room temperature for 2–3 hrs. The resultant solution was filtered to remove solid matter, and the filtrate was dried using a flash evaporator at a temperature of lower than 45° C. to produce about 100 g of a solid extract. This solid extract was then extracted three times with 0.5 L of ethyl acetate. The resultant liquid extracts were combined and concentrated under reduced pressure to produce an enriched solid extract. To the resultant solid extract, 0.3 L of methanol was added to produce a liquid extract. This step was repeated three times. The liquid extracts were combined and dried using a flash evaporator and another solid extract was obtained (20 g). 0.2 g of the solid extract was subsequently passed through a solid phase extraction column (SepPak $C_{18}$, 2 cm×4 cm). After flushed with 100 mL of a 50% aqueous methanol, and then 100 mL of a 50% aqueous acetonitrile, the column was eluted with an 80% aqueous acetonitrile. The fractions containing epoxyvibsanin B were collected and dried under reduced pressure to produce solid matter. Then the column was eluted again with the developing solvent to produce additional epoxyvibsanin B. The solid matter (100 mg) was further purified with a HPLC column (Waters $C_4$ ID 50×300 mm) with 10–50% acetonitrile-water as the developing solvent. The fractions containing epoxyvibsanin B were collected and concentrated under reduced pressure to obtain 5.2 mg of white powder. (m.p. 100–102° C.); $\lambda_{max}$ 221 nm (acetonitrile); HREIMS m/z 417.2626 (C25H3705); $^1$H NMR, see Table 1.

TABLE 1

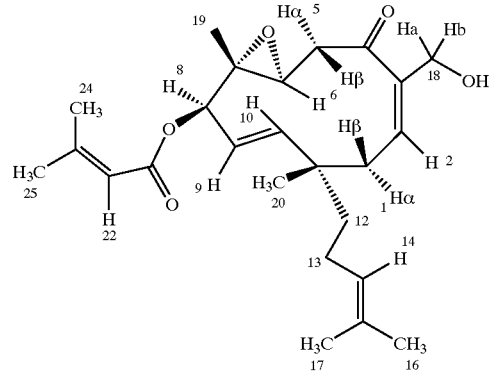

Full Assignment of Epoxyvibsanin B (300 MHz $^1$H NMR)

| Chemical Shift (δ ppm) | Proton Number | Coupling Pattern | Coupling Constant (Hz) | Position Assigned |
|---|---|---|---|---|
| 1.02 | 3H | s | | 20 |
| 1.39 | 1H | ddd | 4.6, 11.7 and 15.1 | 12a |
| 1.26 | 1H | m | | 12b |
| 1.57 | 3H | s | | 17 |
| 1.66 | 3H | s | | 16 |
| 1.80 | 2H | m | | 13 |
| 1.45 | 3H | s | | 25 |
| 1.97 | 1H | dd | 11 and 7 | 1α |
| 2.62 | 1H | dd | 11 and 7 | 1β |
| 2.14 | 3H | d | 1.2 | 25 |
| 1.89 | 3H | s | | 19 |
| 4.17 | 1H | d | 14 | 18a |
| 4.48 | 1H | dd | 14 and 1.2 | 18b |
| 3.19 | 1H | dd | 4.7 and 18 | 5α |
| 3.39 | 1H | d | 4.7 amd 18 | 5β |
| 2.74 | 1H | dd | 18 and 13 | 6 |
| 5.75 | 1H | dd | 11.7 and 7 | 2 |
| 5.05 | 1H | t | 7 | 14 |
| 5.07 | 1H | d | 13.5 | 8 |
| 5.32 | 1H | dd | 16.4 and 13.5 | 9 |
| 5.69 | 1H | d | 16.4 | 10 |
| 5.70 | 1H | brs | | 22 |

IL-12 Inhibitory Assays

Mononuclear cells from human peripheral blood (PBMC) were harvested from a leukopak using standard procedures. The cells, diluted to three millions per mL, were maintained in RPMI medium supplemented with fetal calf serum (10%), penicillin (100 U/mL), streptomycin (100 μg/mL) and L-glutamate (2 mM). Human interferon gamma (IFN-γ, Boehringer Mannheim; catalog no. 1040596) was diluted to 60 units/mL using the cell-containing supplemented medium. 100 μL of the resulting cell culture was added to each well of a 96-well U-shaped bottom microtiter plate, and incubated overnight in a humidified 37° C., 7% $CO_2$ incubator. Epoxyvibsanin B in 4×RPMI stock medium was added to each well with a final concentration of 1 μg/mL, followed by the addition of lipopolysaccharide (LPS, Serratia arscencens Sigma; catalog no. L-4766) in 4×RPMI stock medium with a final concentration of 1 μg/mL. The plate was gently vortexed and continuously incubated for 16 hrs. IFN-γ and LPS have stimulated PBMC for IL-12 production. The supernatant from each cell culture was harvested, and the secreted IL-12 p70 in the supernatant was quantitated with a sandwich ELISA using anti-human IL-12 antibodies (R & D systems; catalog no. mAb 611 and catalog no. BAF 219). An epoxyvibsanin B-free control experiment was also perfonned. The results show that epoxyvibsanin B inhibited 90% of IL-12 production, as compared with that of the control experiment.

The inhibition of IL-12 production was further tested in parallel experiments using two cell lines: PBMC and the human promonocytic leukemia mononuclear cells (THP-1 cells). As described above, PBMC were added to a 96-well plate with 500,000 cells per well, and stimulated for IL-12 production with IFN-γ (200 U/ml) and LPS (1 µg/ml). In parallel, THP-1 cells were added to a 96-well plate with 800,000 cells per well, and stimulated for IL-12 production with IFN-γ (2000 U/ml) and Staph Aureus Cowan I (0.05%, SAC or Pansorbin; from Calbiochem; lot no. B15921). The supernatant from each cell culture was harvested and analyzed for IL-12 p70 with a sandwich ELISA by using the antibodies indicated above. The results show that epoxyvibsanin B inhibited IL-12 production in both PBMC and THP-1 cells. It had an $IC_{50}$ of about 1 nM for the PBMC and an $IC_{50}$ of 20 nM for the THP-1 cells. The activity of epoxyvibsanin B in inhibiting IL-12 production is 10-fold that of a known anti-inflammatory compound, dexamethazone.

Cytotoxicity Assay

Epoxyvibsanin B was also tested for cytotoxicity using a Cell Titer 96 Aqueous Non-radioactive kit (Promega, order no. G5421). Phenazine methosulfate (Sigma; catalog no. P 5812) was added as an electron donor to a cell culture containing PBMC (500,000 cells per well) and epoxyvibsanin B (final concentration of 1 µg/ml). 3-(4,5-Dimethylthiazole-2-yl)-5-(3-carbomethoxyphenyl)-2-(4-sulphophenyl)-2H-tetrazolium (MTS) was then added. Cells were incubated for 2 hours in a humidified 37° C., 7% $CO_2$ incubator. The supernatant from the cell culture was harvested and its absorbance at 490 nm was recorded. Cell viability was determined based on the level of MTS (which reacted with mitochondria dehydrogenases enzymes in the living cells), as compared to that obtained from an epoxyvibsanin B-free control experiment. Epoxyvibsanin B was further tested for cytotoxicity toward THP-1 cells. The results show that epoxyvibsanin B had similar cytotoxicity toward both PBMC and THP-1 cells. It had a $CC_{50}$ of 5 µM for PBMC, and a $CC_{50}$ of 10 µM for THP-1 cells. The cytotoxicity of epoxyvibsanin B is lower than that of dexamethazone, an anti-inflammatory compound.

OTHER EMBODIMENTS

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to epoxyvibsanin B also can be made, screened (e.g., by the methods described in the above examples), and used to practice the present invention. Thus, other embodiments are also within the claims.

What is claimed is:

1. A compound of the following formula:

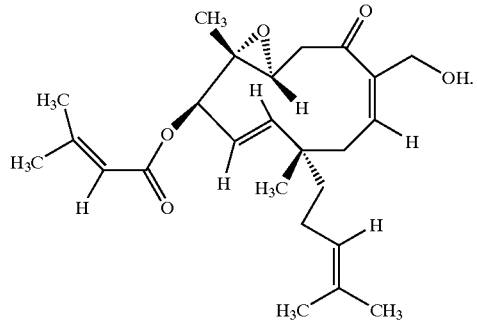

2. A pharmaceutical composition comprising the compound of claim 1 and a pharmaceutical acceptable carrier thereof.

3. A method for treating an interleukin-12 overproduction-related disorder, comprising administering to a subject in need thereof an effective amount of the compound of claim 1.

4. The method of claim 3, wherein the disorder is an inflammatory disease.

5. The method of claim 4, wherein the inflammatory disease is an autoimmune disease.

* * * * *